(12) United States Patent
Castro

(10) Patent No.: US 10,932,919 B2
(45) Date of Patent: Mar. 2, 2021

(54) SPINAL IMPLANT SYSTEM

(71) Applicant: BLUE SKY TECHNOLOGIES, LLC, Louisville, KY (US)

(72) Inventor: Frank Castro, Louisville, KY (US)

(73) Assignee: BLUE SKY TECHNOLOGIES, LLC, Louisville, KY (US)

( * ) Notice: Subject to any disclaimer, the term of this patent is extended or adjusted under 35 U.S.C. 154(b) by 73 days.

(21) Appl. No.: 16/097,243

(22) PCT Filed: Apr. 3, 2018

(86) PCT No.: PCT/US2018/025782
§ 371 (c)(1),
(2) Date: Oct. 27, 2018

(87) PCT Pub. No.: WO2019/018013
PCT Pub. Date: Jan. 24, 2019

(65) Prior Publication Data
US 2020/0179127 A1    Jun. 11, 2020

Related U.S. Application Data

(60) Provisional application No. 62/534,155, filed on Jul. 18, 2017.

(51) Int. Cl.
| | | |
|---|---|---|
| A61F 2/44 | (2006.01) | |
| A61F 2/46 | (2006.01) | |
| A61B 17/70 | (2006.01) | |
| A61F 2/30 | (2006.01) | |
| A61F 2/42 | (2006.01) | |

(Continued)

(52) U.S. Cl.
CPC .......... *A61F 2/447* (2013.01); *A61B 17/7002* (2013.01); *A61B 17/7059* (2013.01); *A61F 2/44* (2013.01); *A61F 2/4405* (2013.01); *A61F 2/4455* (2013.01); *A61F 2/4603* (2013.01); *A61F 2/4611* (2013.01); *A61B 17/1671* (2013.01); *A61B 2017/00884* (2013.01); *A61F 2/42* (2013.01); *A61F 2/4606* (2013.01); *A61F 2002/30179* (2013.01); *A61F 2002/30266* (2013.01); *A61F 2002/30364* (2013.01); *A61F 2002/30579* (2013.01); *A61F 2002/30593* (2013.01); *A61F 2002/30622* (2013.01); *A61F 2002/30736* (2013.01); *A61F 2002/30845* (2013.01); *A61F 2002/30995* (2013.01); *A61F 2002/449* (2013.01); *A61F 2002/4627* (2013.01); *A61F 2310/00017* (2013.01); *A61F 2310/00023* (2013.01)

(58) Field of Classification Search
CPC ............. A61F 2/4405; A61F 2002/449; A61B 17/7062
See application file for complete search history.

(56) References Cited

U.S. PATENT DOCUMENTS 8,114,135 B2 *  2/2012  Malandain ......... A61B 17/7053
                                                606/263
8,328,870 B2   12/2012  Patel et al.
(Continued)

*Primary Examiner* — Andrew Yang
(74) *Attorney, Agent, or Firm* — Business Patent Law, PLLC; Kenneth F. Pearce

(57) ABSTRACT

A system used for connecting a first implant and a second spinal implant. Among other things, the system includes a connector with a flexible member that allows the connector to be positioned a plurality of angles relative to the first implant.

17 Claims, 5 Drawing Sheets

(51) Int. Cl.
    *A61B 17/16*     (2006.01)
    *A61B 17/00*     (2006.01)

(56) References Cited

U.S. PATENT DOCUMENTS

| | | |
|---|---|---|
| 8,702,733 B2 | 4/2014 | Ferree |
| 8,979,903 B2 | 3/2015 | Capote et al. |
| 8,979,933 B2 | 3/2015 | Vishnubholta et al. |
| 9,039,770 B2 | 5/2015 | Aferzon et al. |
| 9,283,084 B1 | 3/2016 | O'Hara |
| 2005/0277934 A1 | 12/2005 | Vardiman |
| 2007/0149978 A1 | 6/2007 | Shezifi et al. |
| 2010/0145386 A1 | 6/2010 | Greenhalgh et al. |
| 2014/0046373 A1 | 2/2014 | Brennan |
| 2015/0202051 A1 | 7/2015 | Tanaka et al. |
| 2016/0106478 A1 | 4/2016 | Simpson et al. |
| 2016/0324546 A1 | 11/2016 | Simpson et al. |
| 2016/0324547 A1 | 11/2016 | Miller et al. |

\* cited by examiner

SPINAL IMPLANT SYSTEM

Applicant claims priority to PCT Application entitled—Spinal Implant System—, Serial No. PCT/US2018/025782, filed Apr. 3, 2018 that claimed priority to US provisional Patent Application entitled—Joint Arthrodesis System—, Ser. No. 62/534,155, filed Jul. 18, 2017.

BACKGROUND OF THE INVENTION

A. Field of the Invention

The present invention is a spinal implant system. The current system utilizes a connector to interconnect first and second spinal implants. Among other things, one or more of the implants of the current system can include a cutting edge as well as a rotatable cutter.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

1) U.S. Pat. No. 8,979,903-Capote, et al. discloses a revision fixation plate and method of use. Based on the current record, among other things, Capote, et al. does not disclose a spinal implant system comprising a combination interconnecting a first implant and a second implant; the combination comprising: a) a flexible member connected with the first implant and a connector, wherein the flexible member allows the connector to be positioned at a plurality of angles relative to the first implant; b) a coupler comprising docking areas connected with the connector and the second implant; and c) means securing the connector and the second implant with the docking areas of the coupler.

2) US Published Patent Application No. 20050277-Vardiman discloses a rod delivery device and method. Based on the current record, among other things, Vardiman does not disclose a spinal implant system comprising a combination interconnecting a first implant and a second implant; the combination comprising: a) a flexible member connected with the first implant and a connector, wherein the flexible member allows the connector to be positioned at a plurality of angles relative to the first implant; b) a coupler comprising docking areas connected with the connector and the second implant; and c) means securing the connector and the second implant with the docking areas of the coupler.

3) US Published Patent Application No. 20070149978—Shezifi, et al. discloses a minimally invasive distraction device and method. Based on the current record, among other things, Shezifi does not disclose a spinal implant system comprising a spinal implant system comprising a combination interconnecting a first implant and a second implant; the combination comprising: a) a flexible member connected with the first implant and a connector, wherein the flexible member allows the connector to be positioned at a plurality of angles relative to the first implant; b) a coupler comprising docking areas connected with the connector and the second implant; and c) means securing the connector and the second implant with the docking areas of the coupler.

4) US Patent Application No. 20160106478-Simpson, et al. discloses a surgical system and method. Based on the current record, among other things, Simpson, et al. does not disclose a spinal implant system comprising a combination interconnecting a first implant and a second implant; the combination comprising: a) a flexible member connected with the first implant and a connector, wherein the flexible member allows the connector to be positioned at a plurality of angles relative to the first implant; b) a coupler comprising docking areas connected with the connector and the second implant; and c) means securing the connector and the second implant with the docking areas of the coupler.

5) US Published Patent Application No. 20160324546—Simpson, et al. discloses a spinal construct and methods of use. Based on the current record, among other things, Simpson, et al. does not disclose a spinal implant system comprising a combination interconnecting a first implant and a second implant; the combination comprising: a) a flexible member connected with the first implant and a connector, wherein the flexible member allows the connector to be positioned at a plurality of angles relative to the first implant; b) a coupler comprising docking areas connected with the connector and the second implant; and c) means securing the connector and the second implant with the docking areas of the coupler.

6) US Published Patent No. 20160324547-Miller, et al. discloses a spinal correction system and method. Based on the current record, among other things, Miller does not disclose a spinal implant system comprising a combination interconnecting a first implant and a second implant; the combination comprising: a) a flexible member connected with the first implant and a connector, wherein the flexible member allows the connector to be positioned at a plurality of angles relative to the first implant; b) a coupler comprising docking areas connected with the connector and the second implant; and c) means securing the connector and the second implant with the docking areas of the coupler.

SUMMARY OF THE INVENTION

Numerous surgical procedures in the cervical spine involve removing bone. Whenever bone is removed, the likelihood of a spinal instability is increased.

The current spinal implant system can interconnect a first and a second spinal implant. Unlike other current spinal surgical procedures, a connector interconnecting the first and second spinal implants can be manipulated through a plurality of angles relative to the first spinal implant.

By way of illustration, an open door laminoplasty surgery involves completely cutting through the bone on one side of the spinal column and half way through the lamina on the other side. The posterior arch (laminae and spinous process) are then rotated through the partial fracture to decompress the spinal cord, i.e, the open door laminoplasty is similar to opening a door around a hinge. Prior state-of-the-art procedures utilize screws and small plates to maintain an achieved spinal decompression.

Among other things, the current invention can stabilize the cervical spine by anchoring the first spinal implant through interconnection with other spinal structures. For example, when a patient has spinal stenosis, surgical removal of the lamina, in part or in whole, may not allow adequate decompression of the spinal cord, and the spinal column can be unstable. Use of the current spinal implant system tethers the first implant anchored in a joint to a connector that is connected with a second spinal implant attached to other bony elements of the spinal column. As indicated previously, prior to fixation of the first and second spinal implants, the tether allows the connector to be manipulated through a plurality of angles relative to the first implant.

The more tools or instruments inserted into a surgical field, the greater the possibility of an error or patient injury may occur. Due to the simplicity of the current spinal implant system, a number of surgical tools required and steps associated with performing prior state-of-the-art surgeries can be eliminated. It is anticipated that the current spinal implant system can be utilized in arthrodesis procedures for the cervical spine, sacroiliac joint or other similar joints.

One of the currently available state-of-the art techniques for cervical fusions is the DTRAX system. The DTRAX spinal system uses five instruments, a working cannula, and numerous steps. A working cannula with a chisel is used to breach the desired posterior facet joint. Once in position, the chisel is removed and a broach is inserted through the working cannula. The broach is advanced and retracted several times in order to remove the cartilaginous end-plates. After the broach is removed from the working cannula, a drill is inserted. After drilling is completed, a second rasp is placed to decorticate the posterior cortex. After the use of the second rasp is completed, the fixation device (filled with graft material) is inserted through the working cannula into the joint. Additional graft material is then impacted behind the implant.

Current state-of-the-art sacroiliac surgical procedures require a fusion device that is either inserted from a posterior or lateral approach. Applicant's understanding is: there are fusion devices for use with either the posterior approach or the lateral approach, but the same fusion device is incapable for use with both the posterior and the lateral approaches. Many of the current sacroiliac fusion procedures require the use of working cannulas, numerous broaches, rasps, drills and other devices that tend to complicate the surgical procedure. Applicant's current joint arthrodesis system can accomplish sacroiliac fusions through either a posterior or lateral approach with fewer surgical tools and steps.

An aspect of the present invention is to provide a biocompatible surgical implant system requiring the use of less tools in the surgical field than prior surgical fusion procedures.

Still another aspect of the present invention is to provide a surgical implant system interconnecting a first spinal implant implanted in a first surgically creative cavity with a second implant in a second implant space.

It is still another aspect of the present invention to provide a spinal implant system including a connector for connecting a first and second implant.

Yet still another aspect of the present invention is to provide a spinal implant system, where prior to fixation of the first and second implant to a joint or a bone, the connector can be manipulated through a plurality of angles relative to the first implant.

Still another aspect of the present invention is to provide a spinal implant system that can be utilized with, among other things, cages, plates, poly axial connectors, rods, screws or wedges.

It is still another aspect of the present invention to provide flexible members manufactured from, including but not limited to, biocompatible materials such as fabrics, silicone, polyurethane, silicone-polyurethane copolymers, polymeric rubbers, polyolefin rubbers, elastomers, rubbers, thermoplastic elastomers and/or elastomeric compositions.

A preferred embodiment of the current invention can be described as a spinal implant system; the system comprising: a) a first implant implanted into a first surgically created implant space; the first implant comprising a cutter rotatable by a shaft; the cutter comprising one or more cutting blades, wherein each cutting blade comprises edges for cutting in clockwise and counterclockwise directions; b) a second implant attached to a second implant space, wherein the second space is distinct from the first surgically created implant space; c) a combination interconnecting the first implant and the second implant; the combination comprising: i) a connector comprising external threads, a first aperture at a first end, a second aperture at a second end opposite the first end; ii) a flexible member allowing the connector to be positioned at a plurality of angles relative to the first implant prior to interconnection of the first implant and the second implant; the flexible member connected with the shaft proximate the first end and an internal wall proximate the second aperture such that movement of the flexible member is adapted to rotate the shaft; and iii) a coupler comprising a threaded aperture engaging the external threads and an opening adapted to receive a portion of the second implant; d) one or more fasteners securing the coupler to the external threads; and e) means securing the coupler with the second implant.

Another preferred embodiment the current invention can be described as a spinal implant system; the system comprising: a) a first implant implanted into a first surgically created implant space; the first implant comprising a cutter rotatable by a shaft; b) a second implant attached to a second implant space; c) a combination interconnecting the first implant and said second implant; the combination comprising: i) a connector comprising: external threads, a first aperture at a first end, a second aperture at a second end opposite the first end; ii) a flexible member allowing the connector to be positioned at a plurality of angles relative to the first implant; the flexible member connected with the shaft and the connector; and iii) a coupler comprising a threaded aperture engaging the external threads and an opening adapted to receive a portion of the second implant; and d) means securing the coupler to the external threads and to the second implant.

Still another preferred embodiment the current invention can be described as a spinal implant system; the system comprising: a) a first implant implanted into a first surgically created implant space; b) a second implant attached to a second implant space distinct from the first surgically created implant space; c) a combination interconnecting the first implant and the second implant; the combination comprising: i) a connector comprising: external threads, a first aperture at a first end, a second aperture at a second end opposite the first end; ii) a flexible member allowing the connector to be positioned at a plurality of angles relative to the first implant; the flexible member connected with the first spinal implant and the connector; and iii) a coupler comprising a threaded aperture engaging the external threads and an opening adapted to receive a portion of the second implant; and d) means securing the coupler to the external threads and to the second implant.

Yet another preferred embodiment of the current invention can be described as a spinal implant system comprising a combination interconnecting a first implant and a second implant; the combination comprising: a) a flexible member connected with said first implant and a connector, wherein the flexible member allows the connector to be positioned at a plurality of angles relative to the first implant; b) a coupler comprising docking areas connected with the connector and the second implant; and c) means securing the connector and the second implant with the docking areas of the coupler.

It is the novel and unique interaction of these simple elements which creates the system within the ambit of the present invention. Pursuant to the Articles of the Patent Cooperation Treaty, select preferred embodiments of the current invention follow. However, it is to be understood that the descriptions of the preferred embodiments do not limit the scope of the present invention.

DESCRIPTION OF THE PREFERRED EMBODIMENTS

Figure 1:
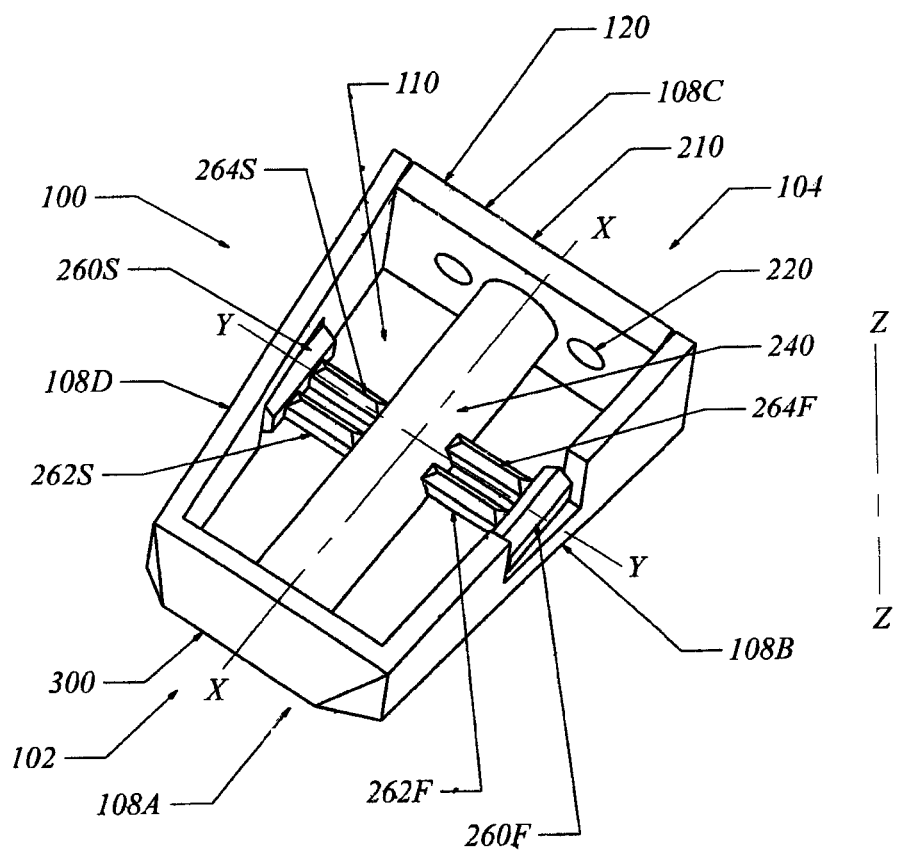
FIG. 1 is a perspective of a preferred embodiment of a first spinal implant (100) compatible with the present spinal implant system.

Although the disclosure hereof is detailed to enable those skilled in the art to practice the invention, the embodiments published herein merely exemplify the present invention.

In the most general sense, the present invention is a spinal implant system where the connector is movable in multiple directions relative to the system's first spinal implant. The current implant can be useful for surgeries that can assist in stabilizing injured, deformed and or degenerative mammalian spines. Preferred embodiments of the current invention can be employed for use in cervical, sacroiliac or other vertebral surgical procedures. It appears that the present system is particularly useful for posterior cervical fusions and sacroiliac joint fusions.

Preferred embodiments of spinal implants and connectors used with current system can be manufactured of titanium alloys, stainless steel, resorbable polymers, non-resorbable polymers or any other composition acceptable in the art. Meeting a long felt but unfilled need in the orthopaedic surgical arts, the novel and unique structures of the present system allow the surgical team to, among other things, simplify previous procedures associated with the interconnection of first and second spinal implants implanted into spine. Within the scope of the present invention, first implants can be provided with one or more cutters, and second implants can include cages, rods or wedges to name a few of the many types of implants compatible with the current spinal implant system.

Devices that insert osteogenic and/or other substances into the interior volume of the spinal implants can be used with the present invention. The current spinal implant system is also compatible with flexible drills, fiber optics, vacuums, one or more cannulas and one or more devices for inserting the spinal implants. Combinations of one or more of the before identified ancillary devices and the current spinal implant system can assist with the creation and healing of the surgical wound.

Openings in some of the spinal implants of current spinal implant system can enhance the probability of the osteogenic materials and/or arthrodesis accelerating substances procuring a blood supply. And it is believed that increasing the blood supply to the osteogenic materials held by the spinal implants of the current system increase the probability of successful fusion. Introduction of osteogenic and other substances into the implant can also hasten the healing of the surgical wound.

Some preferred embodiments of spinal implants of present system can include a cutting edge and a rotatable cutter including one or more blades. Cutting edges associated with some of the system's implants' frameworks are capable of dissecting through adipose, muscle and/or joint capsule tissues. Rotatable cutters of some of the system's implants are capable of cutting cartilage and bone and can be associated with the creation of the surgical cavity. Other spinal implants utilized with the current system do not include cutting edges or rotatable cutters.

Flexible members or tethers of the present spinal implant system can be manufactured from biocompatible materials such as fabrics, silicone, polyurethane, silicone-polyurethane copolymers, polymeric rubbers, polyolefin rubbers, elastomers, rubbers, thermoplastic elastomers and/or elastomeric compositions as wells as other biocompatible materials of adequate tensile strength and flexibility.

FIG. 1 is a perspective of a preferred embodiment of a first spinal implant (100) compatible with the present spinal implant system. Spinal implant (100) has a framework that includes an anterior side (102), surgeon facing or posterior side (104) and a plurality of lengthwise sides (108A-D) extending between anterior side (102) and surgeon facing or posterior side (104). Lengthwise sides (108A, 108C) are provided with opening (110) that, among other things, allows the implant's cutters (260F, 260S) to rotate. When surgical parameters require, osteogenic and/or other substances can also be placed into the internal volume of first spinal implant (100).

As illustrated in FIG. 1, longitudinal axes of the spinal implants of the present system are measured along axis X-X. Axis X-X can correspond with shaft (240), be offset from shaft (240) or correspond with any lengthwise axis of the spinal implant regardless of whether the spinal implant includes a shaft. Widths of spinal implants are measured along axes Y-Y or axes parallel to axis Y-Y as shown in FIG. 1. Heights of the spinal implants are measured along axes Z-Z or axes parallel to axis Z-Z, as shown in FIG. 1, of the spinal implant's framework.

Within the scope of the current invention, select embodiments of spinal implant (100) have a length greater than a width. In select preferred embodiments, the width of spinal implant (100) is greater than the height of spinal implant (100). In other preferred embodiments of spinal implant (100), the height of spinal implant (100) is greater than the width of spinal implant (100). The inward sides of anterior side (102), posterior side (104) and lengthwise sides (108A-D) facing longitudinal axis X-X create an available inner volume of implant (100) which can receive osteogenic as well as other substances.

Lengthwise or lateral sides (108A-108D) are positioned outward from spinal implant's (100) longitudinal axis X-X. Select preferred embodiments of spinal implant (100) are provided with a cross-section distant from anterior side (102) that has a greater cross-sectional area than the anterior side (102). As disclosed herein, cross-sections are determined perpendicular to the longitudinal axis X-X of the spinal implant's framework. Anterior side (102) of implant (100) is provided with cutting edge (300) as will be more specifically enabled below. In some preferred embodiments, cutting edge (300) can be integral with anterior side (102) of spinal implant (100). Attached to shaft (240) are arms (262F, 262S) supporting cutters (260F, 260S). Although as shown in FIG. 1, cutters (260F, 260S) are supported by two arms (262F, 262S), in select preferred embodiments, cutters (260F, 260S) can be supported by a single arm (262F, 262S). Additionally, some preferred embodiments of cutters (260F, 260S) can be provided with one or more sharp edges (264F, 264S) that can assist cutters (260F, 260S) with the morselization of bone.

Posterior side (104) of spinal implant (100) includes cross-sectional area (120). Preferred embodiments of spinal implant (100) are provided with plate (210) where at least a portion the plate (210) is perpendicular to longitudinal axis X-X. Plate (210) is seated within cross-sectional area (120) of surgeon facing side (104) and affixed to implant (100). Preferred embodiments of plate (210) are provided with one or more apertures (220) that can be utilized with one or more instruments associated with the surgery as well as the current system's connector (400).

Figure 2:
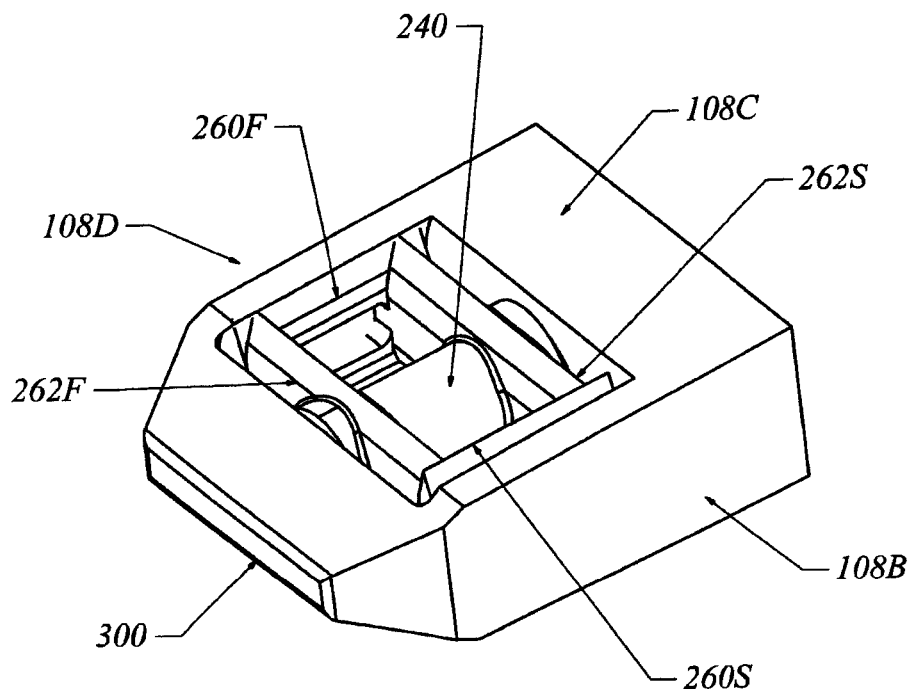
FIG. 2 is perspective of a preferred embodiment of a second spinal implant (100) compatible with the present spinal implant system.

FIG. 2 is perspective of a preferred embodiment of a second spinal implant (100) compatible with the present spinal implant system.

Figure 3:
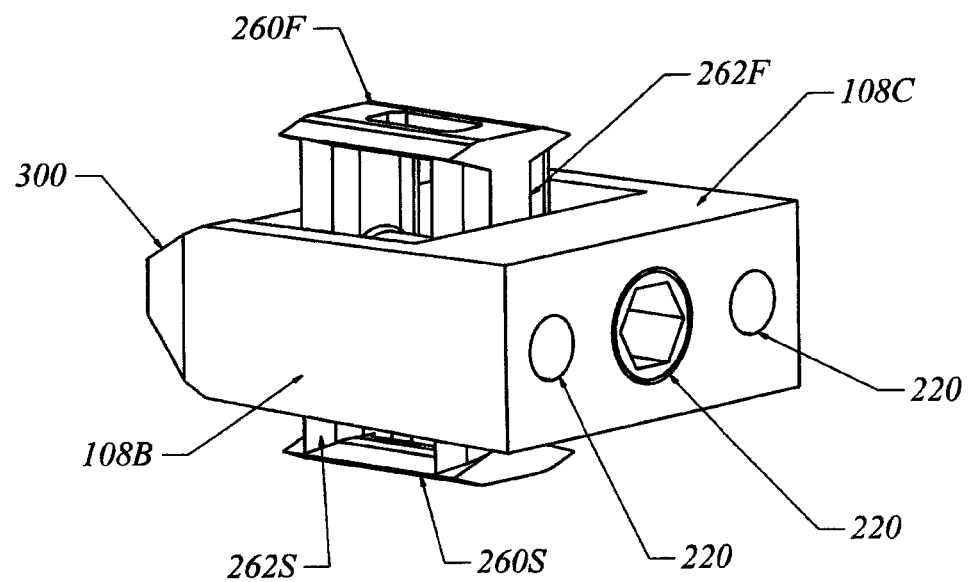
FIG. 3 is another perspective of a preferred embodiment of the second spinal implant (100) compatible with the present spinal implant system.

FIG. 3 is another perspective of a preferred embodiment of the second spinal implant (100) compatible with the present spinal implant system. As shown, when surgical parameters require, cutters (260F, 260S) of the FIG. 3 embodiment can be rotated 360 degrees about opening (110) of implant without contacting lengthwise sides (108A-108D).

As measured along longitudinal axis X-X of the spinal implant's (100) frameworks enabled in FIGS. 1-3, preferred embodiments are provided with cutting edge (300) that can be up to about 3 millimeters in length. Select preferred embodiments of implant (100) have lengths, including cutting edge (300), from about 50 millimeters to about 6 millimeters. Cross-sectional widths of cutting edge (300) can range from about 2 millimeters$^2$ to about 18 millimeters$^2$. Cross-sectional widths of implant (100), other than cutting edge (300) can range from about 8 millimeters$^2$ to about 45 millimeters$^2$.

Figure 4:
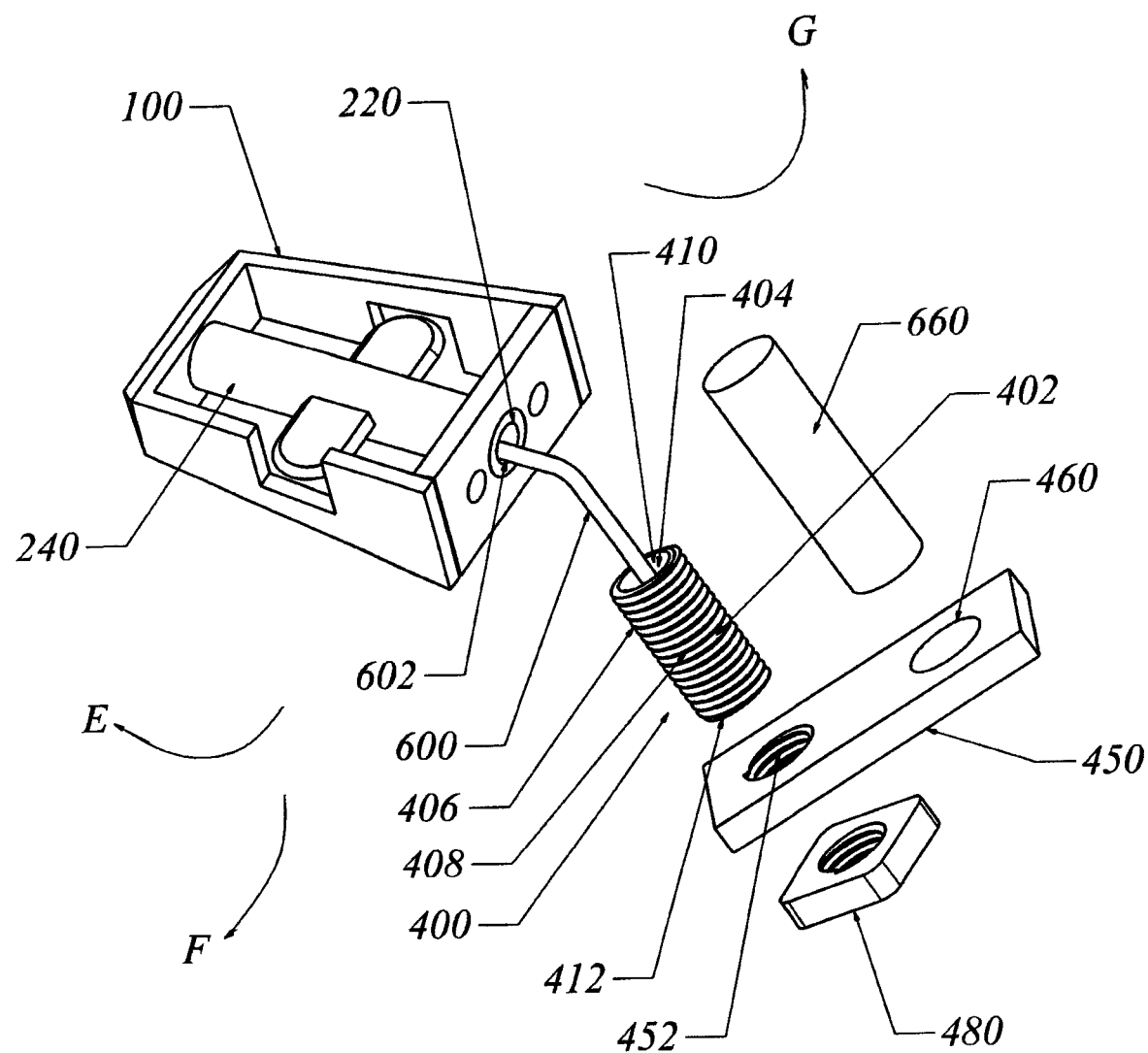
FIG. 4 is an exploded view of a preferred embodiment of the current spinal implant system.

FIG. 4 is an exploded view of a preferred embodiment of the current spinal implant system. The preferred embodiments of spinal implants enabled in FIGS. 1-3 are fully functional with the present spinal implant system enabled in FIG. 4. However, unlike first spinal implant (100) enabled in FIGS. 1-3, the FIG. 4 preferred embodiment is provided with cutters attached directly to shaft (240). Shaft (240) is adapted to rotate cutter in the clockwise and counterclockwise directions.

With a view toward FIG. 4, flexible member or tether (600) extends inward of aperture (220) of spinal implant (100) and is attached to shaft (240). First end (602) of tether (600) is attached to shaft (240) in any manner acceptable in the art. Moving/turning flexible member (600) can rotate shaft (240) of spinal implant (100). Second end (604) of tether (600) is attached to inner side (404) of wall (402) of connector (400). Outer side (406) of wall (402) of connector (400) is provided with threads (408) for engaging coupler (450). Connector (400) can also include first aperture (410) and second aperture (412). Coupler (450) is provided with threaded aperture or docking area (452) for reciprocating with threads (408) of connector (400) and opening or docking area (460) is capable of receiving at least a portion of second implant (660). As shown, fastener (480) can securely attach coupler (450) to connector (400). However, any means acceptable in the art, such as, adhesives, ball and socket joints, clips, mesh or wire fasteners, among others, can be utilized to secure coupler (450) to connector (400). And when surgical perimeters require, opening (460) of coupler (450) can also include threads. Arrows E, F and G portray that connector (400) can be moved in a multitude of angles/directions relative to spinal implant (100).

Figure 5:
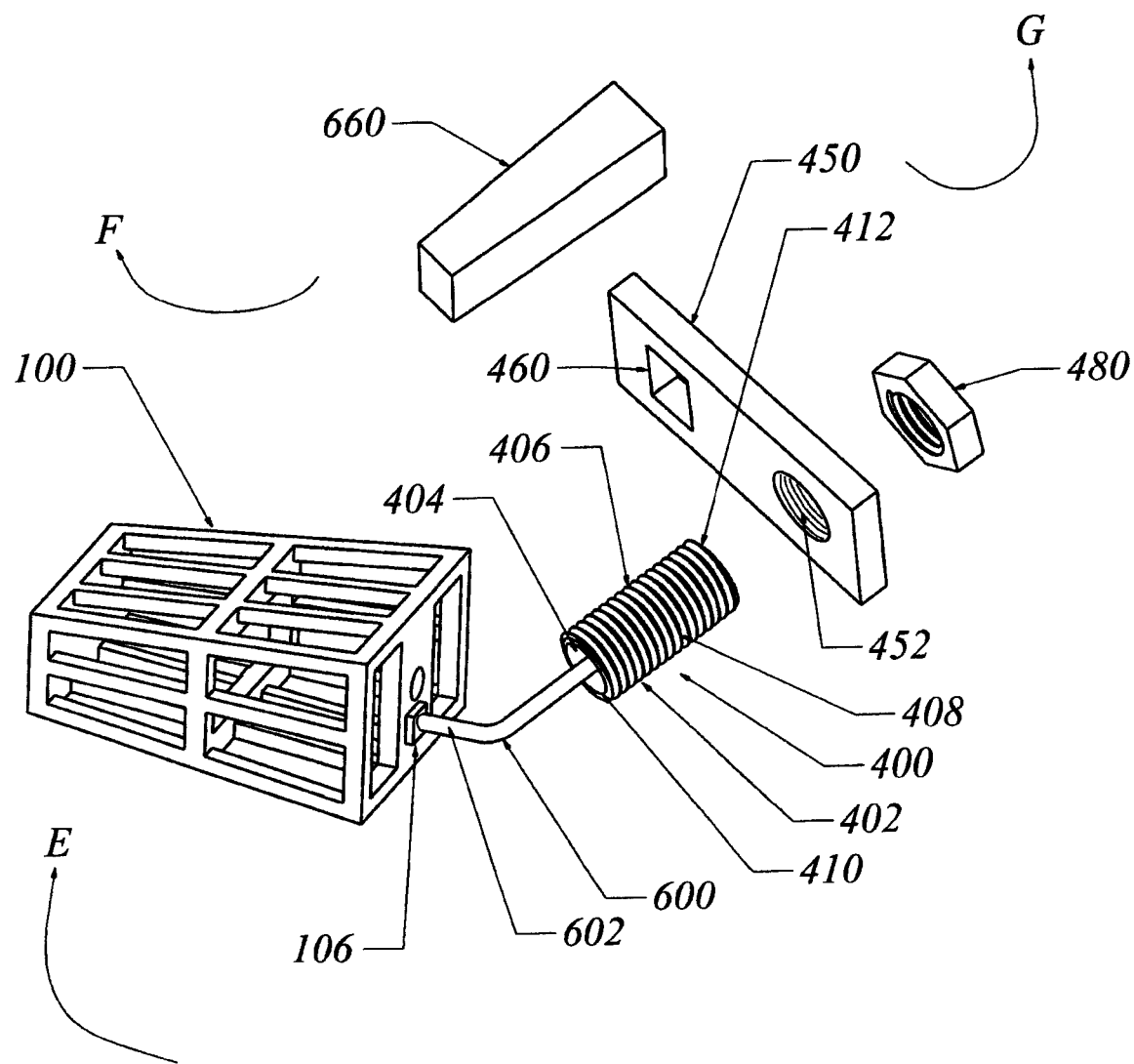
FIG. 5 is an exploded view of a preferred embodiment of the current spinal implant system.

FIG. 5 is an exploded view of a preferred embodiment of the current spinal implant system. Unlike the first spinal implant (100) enabled in FIG. 4, the FIG. 5 preferred embodiment of first spinal implant (100) does not include any cutter or cutting edge. The FIG. 5 preferred embodiment of first spinal implant (100) is fully functional with the current spinal implant system. It is anticipated that other first spinal implants (100) not shown in FIGS. 1-6 are also fully functional with the present spinal implant system. In other words, a first spinal implant connectable with flexible member (600) is compatible with the current spinal implant system.

Tether (600) is attached directly to housing (106) of first spinal implant (100). Depending on surgical perimeters, flexible member (600) can be attached to outward side or inward side of housing or cage (106) of spinal implant (100). First end (602) of tether (600) is attached to housing or cage (106) in any manner acceptable in the art. Second end (604) of tether (600) is attached to inner side (404) of wall (402) of connector (400). Outer side (406) of wall (402) of connector (400) is provided with threads (408) for engaging coupler (450). Connector (400) can also include first aperture (410) and second aperture (412). Coupler (450) is provided with threaded aperture or docking area (452) for reciprocating with threads (408) of connector (400) and opening or docking area (460) is capable of receiving at least a portion of second implant (660). Fastener (480) securely attaches coupler (450) to connector (400). However, any means acceptable in the art, such as, adhesives, ball and socket joints, clips, mesh or wire fasteners, among others, can be utilized to secure coupler (450) to connector (400). And when surgical perimeters require, opening (460) of coupler (450) can also include threads. Arrows E, F and G portray that connector (400) can be moved in a multitude of angles/directions relative to spinal implant (100).

The second implant (660) depicted in FIG. 4 is a rod and the second implant (660) depicted in FIG. 5 is a wedge or a cage. Although not shown in the drawings, other second implants (660) such as poly axial connectors, plates and screws are within the scope of the present system. Any means acceptable in the art can be used to attach second implant (660) to opening (460) of coupler (450).

In accordance with the current spinal implant system, connector (400) can be from about three to about twelve millimeters in its each of geometric dimensions of height, width and/or length. Within the above of the current system, dimensions for coupler (450) can include: a thickness of from about one millimeter to about four millimeters; a width of from about four to about ten millimeters; and a length from about ten millimeters to about 200 millimeters in length.

Figure 6:
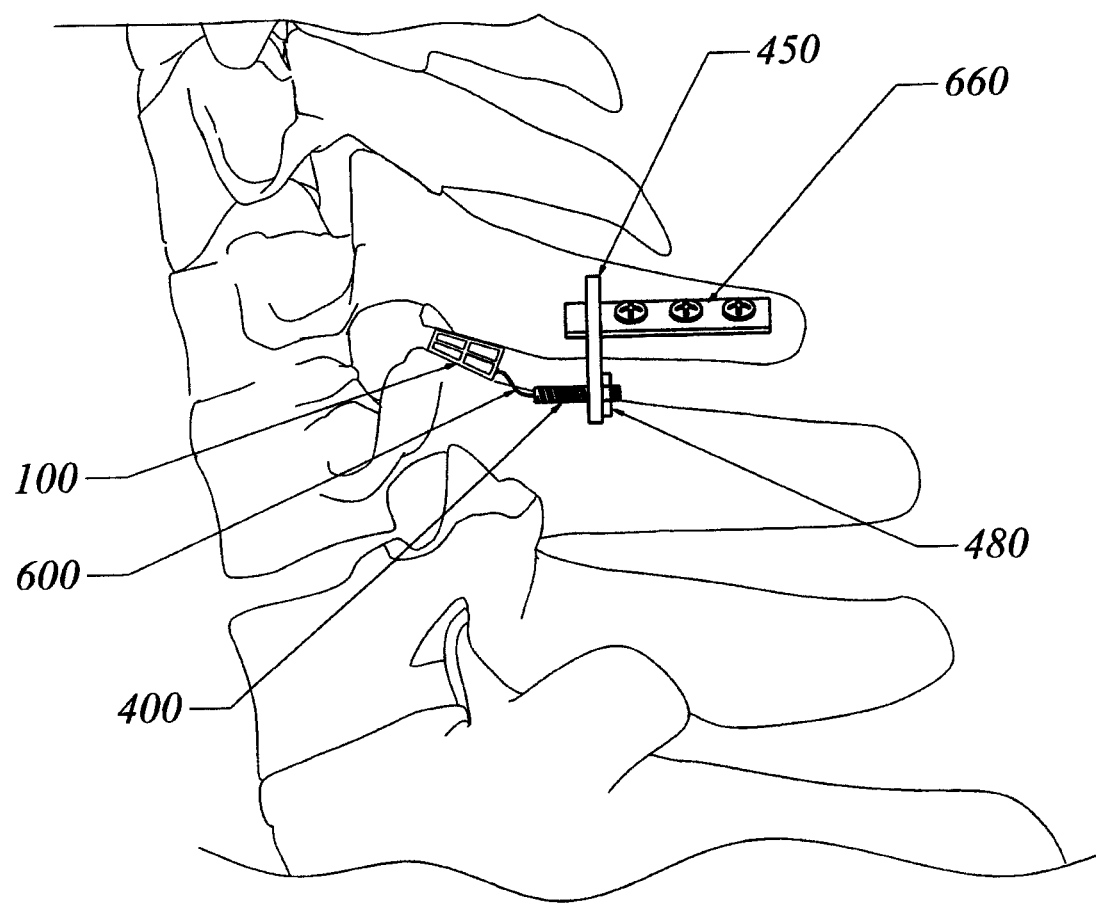
FIG. 6 is a perspective of an example of the present spinal system utilized in the vertebral column.

FIG. 6 is a perspective of an example of the present spinal system utilized in the posterior cervical column. Connector (400) and coupler (450) interconnect first spinal implant (100) with second spinal implant (660). As shown, first spinal implant (100) is implanted into a surgically created space in the facet joint between the fifth and sixth vertebral bodies and second implant (660) is implanted in a second implant space. By way of illustration and not limitation, FIG. 6 portrays a spinal surgical procedure where second implant (660) is anchored to the spinous process of C5 with three fixation screws. Although not shown in FIG. 6, one or more first spinal implants (100), connectors (400) and second spinal implants (660) can be utilized to interconnect one or more first surgically created spaces and one or more second implant spaces.

Pursuant to the Articles of the Patent Cooperation Treaty, preferred embodiments of the current system invention have been disclosed and enabled.

What is claimed is:

1. A spinal implant system; said system comprising:
   a) a first implant configured for implantation into a first surgically created implant space; said first implant comprising an anterior cutting edge and a cutter rotatable by a shaft; said cutter comprising one or more cutting blades, wherein each cutting blade comprises edges for cutting in clockwise and counterclockwise directions;
   b) a second implant adapted for attachment to a bony element, wherein said bony element is distinct from said first surgically created space;
   c) a combination interconnecting said first implant and said second implant; said combination comprising:
      i) a connector comprising external threads, a first aperture at a first end, a second aperture at a second end opposite said first end;
      ii) a flexible member allowing said connector to be positioned at a plurality of angles relative to said first implant prior to interconnection of said first implant and said second implant; said flexible member connected with said shaft proximate said first end and an internal wall proximate said second aperture such that movement of said flexible member is adapted to rotate said shaft; and
      iii) a coupler comprising a threaded aperture engaging said external threads and an opening adapted to receive a portion of said second implant;
   d) one or more fasteners securing said coupler to said external threads; and
   e) means securing said coupler with said second implant.

2. The spinal implant system of claim 1, wherein said anterior cutting edge is straight.

3. The spinal implant system of claim 2, wherein said second implant is a cage, plate, poly axial connector, rod, screw or wedge.

4. A spinal implant system; said system comprising:
   a) a first implant configured for implantation into a first surgically created space; said first implant comprising an anterior cutting edge and a cutter rotatable by a shaft, wherein said cutter comprises at least one cutting blade for cutting in clockwise and counterclockwise directions;
   b) a second implant adapted for attachment to a bony element;
   c) a combination interconnecting said first implant and said second implant; said combination comprising:
      i) a connector comprising: external threads, a first aperture at a first end, a second aperture at a second end opposite said first end;
      ii) a flexible member allowing said connector to be positioned at a plurality of angles relative to said first implant; said flexible member connected with said shaft and said connector; and
      iii) a coupler comprising a threaded aperture engaging said external threads and an opening adapted to receive a portion of said second implant; and
   d) a fastener device distinct from said external threads and said coupler securing said coupler to said external threads and to said second implant.

5. The spinal implant system of claim 4, wherein said anterior cutting edge is straight.

6. The spinal implant system of claim 5, wherein said second implant is a cage, plate, poly axial connector, rod, screw or wedge.

7. The spinal implant system of claim 6, wherein movement of said flexible member is adapted to rotate said shaft.

8. A spinal implant system; said system comprising:
   a) a first implant comprising an outer straight anterior cutting edge and an rotatable cutter adapted to cut in clockwise and counterclockwise directions; said first implant configured for implantation into a first surgically created space, wherein said first surgically created space receives at least a portion of said first implant;
   b) a second implant adapted for attachment to a bony element distinct from said first surgically created space;
   c) a combination interconnecting said first implant and said second implant; said combination comprising:
      i) a connector comprising: external threads, a first aperture at a first end, a second aperture at a second end opposite said first end;
      ii) a flexible member allowing said connector to be positioned at a plurality of angles relative to said first implant; said flexible member connected with said first spinal implant and said connector;
      iii) a coupler comprising a threaded aperture engaging said external threads and an opening adapted to receive a portion of said second implant; and
   d) means securing said coupler to said external threads and to said second implant.

9. The spinal implant system of claim 8, wherein said first spinal implant comprises an internal volume; includes a rotatable shaft and one or more cutters connected to said rotatable shaft.

10. The spinal implant system of claim 9, wherein said flexible member is attached to said rotatable shaft and said connector.

11. The spinal implant system of claim 10, wherein said second implant is a cage, plate, poly axial connector, rod, screw or wedge.

12. A spinal implant system comprising a combination interconnecting a first implant comprising a structure including at least eight outward right angles and a second implant; said combination comprising:
   a) a flexible member attached to said first implant and a connector comprising external threads, wherein said first implant comprises an anterior straight cutting edge and said flexible member allows said connector to be positioned at a plurality of angles relative to said first implant;
   b) a coupler comprising docking areas; said coupler attached to said connector and said second implant; and
   c) a fastener device distinct from said connector and said coupler; the fastener device securing said connector with said coupler.

13. The spinal implant system of claim 12, wherein:
   a) said connector comprises: threads and first and second opposed apertures; and
   b) said coupler comprises threaded docking area adapted to engage said threads.

14. The spinal implant system of claim 13, wherein said first spinal implant (100) comprises a cutting edge.

15. The spinal implant system of claim 14, wherein said first spinal implant (100) comprises an internal volume, a rotatable shaft and a cutter rotatable in clockwise or counterclockwise directions.

16. The spinal implant system of claim 15, wherein said flexible member is attached to said rotatable shaft.

17. The spinal implant system of claim 16, wherein said second implant is a cage, plate, poly axial connector, rod, screw or wedge.

* * * * *